United States Patent [19]

Jacob

[11] Patent Number: 5,858,372
[45] Date of Patent: Jan. 12, 1999

[54] HERBAL MEDICATION FOR THE TREATMENT OF PSORIASIS

[76] Inventor: George Jacob, 7106 NW 11th Pl., Gainesville, Fla. 32605

[21] Appl. No.: 928,959

[22] Filed: Sep. 12, 1997

[51] Int. Cl.$^6$ .................................................. A01N 65/00
[52] U.S. Cl. ........................ 424/195.1; 424/400; 424/58; 424/59; 424/78.05
[58] Field of Search ................................ 424/195.1, 400, 424/58, 59, 78.05

[56] References Cited

U.S. PATENT DOCUMENTS

| | | |
|---|---|---|
| 3,981,996 | 9/1976 | Leigh . |
| 4,769,390 | 9/1988 | Roelz et al. . |
| 4,826,677 | 5/1989 | Mueller et al. . |
| 4,857,554 | 8/1989 | Kallimanis . |
| 5,624,915 | 4/1997 | Gallina . |
| 5,723,139 | 3/1998 | Granger et al. . |

OTHER PUBLICATIONS

Sethuraman et al, Antiinflammatory Activity of Wrightia Tinctoria Flowers, Indian Drugs 22(3), 158–9, 1984.

*Primary Examiner*—Thurman K. Page
*Assistant Examiner*—Brian K. Seidleck
*Attorney, Agent, or Firm*—Draughon P.A.

[57] ABSTRACT

A pharmaceutical preparation for topical treatment of skin disorders, particularly psoriasis, comprising the ingredients of a latex extracted from the leaves of the *Wrightia tinctoria* R Br. plant, urea, and polyethylene glycol. The pharmaceutical preparation is also a hydrophilic ointment that is capable of delivering the active drugs without being greasy or irritating to the skin.

18 Claims, No Drawings

HERBAL MEDICATION FOR THE TREATMENT OF PSORIASIS

BACKGROUND

Psoriasis is among the dermatoses having a poorly understood etiology. The ailment is a chronic skin disease usually occurring in early to middle age and affecting approximately 2% of the US population. Psoriasis is characterized by epidermal hyperplasia and a greatly accelerated rate of epidermal turnover. The lesions are characteristically dry, well demarcated, red, slightly raised and scaly. Gentle scraping of the lesion removes scales and produces many pinpoint bleeding sites, the so-called "Auspitz sign". The lesions are discrete or confluent erythromatous plaques and papules covered with white or silvery scales found on the extensor surfaces such as the elbows, knees, back and scalp. No part of the body is exempt. The lesions may be localized or generalized.

The therapies of choice are generally limited to the topical application of fluorinated corticosteriods, keratolytics containing salicylates, coal tar, anthralin preparations and systemic therapy with corticosteroids and methotrexate. Methotrexate and drugs like it have severe side effects such as bone marrow depression and thus their therapeutic benefits must be weighed against potentially dangerous side effects. In addition, the formulations to be used are limited to the most common preparations such as, solutions, creams, and salves. Consequently, the manner of application for the dermatherapy is practically predetermined.

Typically the only pharmaceutical forms in which the therapeutic agents are available are lipophilic preparations for local therapy, due to the high instability of the active ingredients against air, oxygen, water, and alkalis. The strongly fattening lipophilic preparations have relatively low storage stability. Such preparations are necessarily inconvenient to use because the hydrophobic preparations are difficult to wash off.

A hydrophilic pharmaceutical preparation capable of delivering a therapeutic agent for the treatment of psoriasis is needed. The preparation would also need to have a high storage stability, and be innocuous, and non irritating to the skin. A therapeutic agent that is nontoxic and effective in treating psoriasis is also needed.

SUMMARY OF THE INVENTION

The hydrophilic ointment of the present invention includes a latex extract derived from the leaves of the *Wrightia tinctoria* R. Br. plant, urea and polyethylene glycol. The affected area of the cutis is treated topically by the application of the ointment to the skin. The hydrophilic ointment is water soluble, and innocuous, does not irritate the skin and is non-greasy. The ointment is also free of parabens, which may sensitize or irritate the skin.

The first principle component of the hydrophilic ointment of the present invention is the latex extract derived from the leaves of the *Wrightia tinctoria* R. Br. plant. The *Wrightia tinctoria* R. Br. plant is a small genus of shrubs or small trees distributed in tropical Asia and Australia. The latex derived from the leaf is believed to contain the active ingredient responsible for the beneficial effects of the present invention. The leaf extract has a bluish tint and is a common source for indigo dye. Photochemical analysis of the leaf extract has revealed that it has the following chemistry:

| | |
|---|---|
| β amyrin | Hexane 8% |
| Ursolic acid | Benzene 1.60% |
| Triterpene acid | Chloroform 1.07% |
| | Alcohol 58.60% |

The second principle component of the hydrophilic ointment of the present invention is urea. Urea is represented by the molecular formula $CO(NH_2)_2$ or $CH_4N_2O$, and is a product of protein metabolism. Urea is commercially available as colorless to white, prismatic crystals or as a white crystalline powder. Commercial urea has almost no odor with a cooling saline taste. It is also soluble in water and neutral to litmus.

Urea is the chief nitrogenous constituent in human urine. As a pharmaceutical component in the present invention urea is primarily used topically to remove excess keratin from dry skin. Urea is a protein denaturant that promotes hydration of keratin and mild keratolysis in dry and hyperkeratotic skin. Urea can also be used as an osmotic diuretic, to promote the healing of infected wounds and as an antiseptic.

The third principle component of the hydrophilic ointment of the present invention is polyethylene glycol. Polyethylene glycol is represented by the generic molecular formula of $HO-CH_2(CHOCH_2)_nCH_2OH$, where n=3 to 200. Polyethylene glycol is a wax like solid that is nonvolatile with a melting point between 58°–62° C. Polyethylene glycol is also water soluble and is chemically inert. Patch tests have shown that polyethylene glycol compounds are innocuous and that continued use will not cause skin irritation.

DETAILED DESCRIPTION

The present invention includes a composition comprising a latex extracted from the leaves of the *Wrightia tinctoria* R. Br. plant, water, urea, and polyethylene glycol. The composition is a herbal medication for the treatment of non specific skin diseases, including, but not limited to psoriasis. The composition is topically applied to the affected area of the dermis in order to treat the diseased skin. Other diseases treated by the present invention include, but are not limited to, eczema, dermatitis, herpetic conditions, acne and more generally, diseases having the symptoms of erythema, edema, inflammation, papules, vesicles, macules, pustules, scaling, cracking, crusting and lesions.

The latex component of the present invention is extracted from the leaves of the *Wrightia tinctoria* R. Br. plant. The *Wrightia tinctoria* R. Brown var. laevis is a tree which can grow up to 40 meters tall and has a dark gray bark. The stalk at which the leaf is attached is approximately 5–7 mm long supporting an oblong leaf blade. The tree can be commonly found growing in mountain forests and valley thickets from an elevation of 200 to 1000 meters. The tree is native to, India, Indonesia, Laos, Malaysia, Myarmar, Philippines, Thailand, Vietnam, and Northern Australia. Within the regions where the plant is found the indigenous population has used the entirety of the plant for various reasons. Such uses include, utilizing the roots and leaves for the treatment of injury and cuts, the fruits to cure pulmonary tuberculosis, and extracting a blue dye from the leaves.

The latex of the present invention is harvested from the leaves of the *Wrightia tinctoria* R. Br. plant. The harvested leaves are preferably collected as only fresh healthy leaves from the plant. Once collected, the leaves are cleaned with purified or filtered water and are then diced into smaller pieces. The cut leaves are combined with approximately an equal part of purified or filtered water. The combination of cut leaves and purified water are preferably mixed in a mechanical churner for approximately 6 hours. Other mechanical means may be employed to aid in the liberation of the latex material from the leaves. The leaves may also be churned for longer or shorter periods than the preferred 6 hours depending upon the churning process and the volume of the mixture.

Once churned, the leaf and water mixture form a slurry that is transferred to holding pans. The pans are preferably made of stainless steel and are configured so as to expose the greatest practical surface area of the slurry contained in the pan to a light source. Preferably the light source is the sun, but the light source can be any light emitting device comprised of wavelengths between 300–900 nm. Preferably, the slurry should be uniformly spread over the entire surface of the pan and have a sufficient thickness so as not to allow the slurry to completely dehydrate. The slurry is exposed to a light source for approximately 6 to 8 hours a day for three consecutive days. The mixture should be protected from contaminants while resting within the pans. Such protection may include a wire net cage or transparent covering placed over the pans, but any covering that permits the latex to be exposed to direct sunlight would be appropriate. Once the slurry has been exposed to direct sunlight it is removed from the pans as a concentrated slurry. The concentrated slurry is then strained or filtered to remove any particle aggregates, such as leaf stock, to produce a drug substance.

The drug substance is added slowly and mixed with urea. The urea is preferably of a pharmaceutical grade represented by the molecular formula $CO(NH_2)_2$ or $CH_4N_2O$, has a molecular weight of 60.06, is freely soluble in water, and has a melting point of 132.7° C. Approximately 1 gram of drug substance is slowly added to 100 mg of urea. The drug substance and the urea are slowly mixed until they form a uniform mixture.

Polyethylene glycols are represented by the generic molecular formula $HO-CH_2(CHOCH_2)_nCH_2OH$, where n=3 to 200. The preferred polyethylene glycols of the present invention are polyethylene glycol 3350 and polyethylene glycol 400, with the numbers representing the approximate molecular weight of each polyethylene glycol. The preferred polyethylene glycols are combined and heated to approximately 65° C. or just above the melting point of the combined glycols. Preferably the combined glycols are heated in water bath to a liquid state. The combined glycols are removed from the heat and the uniform mixture is then added to and mixed with the combined glycols until the combined components congeal. The congealed mixture of polyethylene glycol 3350 and polyethylene glycol 400 and uniform mixture of urea and drug substance form a viscous mixture which is the herbal pharmaceutical material of the present invention.

The herbal pharmaceutical material of the present invention can preferably be described as a hydrophilic ointment. The proper quantities of polyethylene glycol 3350 and polyethylene glycol 400 added to the herbal pharmaceutical material of the present invention is determined by the desired texture and consistency of the final product. The polyethylene glycol combination comprises the bulk of the hydrophilic ointment. The solubility of the herbal pharmaceutical material can be increased with the addition of stearyl alcohol. Stearyl alcohol is added to the herbal pharmaceutical material until the desired consistency of material is achieved.

The method of application includes topically applying the hydrophilic ointment of the present invention to the affected areas of the dermis. The ointment is preferably applied twice daily, every day, for up to six weeks or until the diseased skin is healed.

As will be apparent to those skilled in the art to which the invention is addressed, the present invention may be embodied in forms other than those specifically disclosed above, without departing from the spirit or essential characteristics of the invention. The particular embodiments of the invention described are therefore to be considered in all respects as illustrative and not restrictive. The scope of the present invention is as set forth in the appended claims rather than being limited to the examples set forth in the foregoing description. Any and all equivalents are intended to be embraced by the claims.

What is claimed:

1. A herbal pharmaceutical material derived from the leaves of a *Wrightia tinctoria* R. Br. plant for topical treatment of skin diseases, comprising:

a) an irradiated latex extracted from the leaves of the *Wrightia tinctoria* R. Br. plant, wherein said irradiated latex is exposed to a light source emitting a light comprised of wavelengths between 300–900 nm for six to eight hours a day, during a three day period;

b) urea; and c) polyethylene glycol.

2. The herbal pharmaceutical material according to claim 1, wherein the irradiated latex extract is prepared by:

a) collecting and cleaning the leaves;

b) dicing and churning the leaves with an equal amount of water for 3 to 9 hours to form a latex slurry;

c) exposing the latex slurry to a light source for six to eight hours a day for three consecutive days; and d) filtering the latex slurry.

3. The herbal pharmaceutical material according to claim 1, wherein urea is added in portions in a total amount of 10% by weight compared to the latex while the urea and the irradiated latex are being mixed to form a uniform mixture.

4. The herbal pharmaceutical material according to claim 1, wherein the polyethylene glycol is a polyethylene glycol 3350 and a polyethylene glycol 400, the polyethylene glycol 3350 and the polyethylene glycol 400 are combined and heated to approximately 65° C. in a water bath to a liquid state to form a combined glycol, the combined glycol is removed from the water bath, the uniform mixture is then added to the combined glycol and allowed to congeal to form the herbal pharmaceutical material.

5. The herbal pharmaceutical material according to claim 1, wherein the solubility of the herbal pharmaceutical material is increased with the addition of stearyl alcohol.

6. A method of preparing a herbal pharmaceutical material derived from the leaves of a *Wrightia tinctoria* R. Br. plant for topical treatment of skin diseases, comprising the following steps of:

a) extracting a latex from the leaves of the *Wrightia tinctoria* R. Br. plant;

b) irradiating the latex extracted from the leaves of the *Wrightia tinctoria* R. Br. plant to a light source emitting a light comprised of wavelengths between 300–900 nm for six to eight hours a day, during a three day period;

c) adding urea to the latex and mixing to form a uniform mixture;

d) heating a polyethylene glycol in a water bath to about 65° C. to form a viscous gel; and e) adding the uniform mixture to the viscous gel and cooling until congealed to form a hydrophilic ointment.

7. The method of claim 6, wherein the steps of extracting and irradiating the latex include:

a) collecting and cleaning the leaves;

b) dicing and churning the leaves with an equal amount of water for 3 to 9 hours to form a latex slurry;

c) exposing the slurry to a light source for six to eight hours a day for three consecutive days; and d) filtering the latex slurry.

8. The method of claim 6, wherein urea is added in an amount of 50 to 150 mg per gram of latex and is added in portions while the urea and the irradiated latex are being mixed to form a uniform mixture.

9. The method of claim 6, wherein the light source is the sun.

10. The method of claim 6, wherein the light source emits an electromagnetic energy comprised of wavelengths between 300–900 nm.

11. The method of claim 6, wherein the polyethylene glycol is a polyethylene glycol 3350 and a polyethylene glycol 400, the polyethylene glycol 3350 and the polyethylene glycol 400 are combined and heated to approximately 65° C. in a water bath to a liquid state to form a combined glycol, the combined glycol are removed from the water bath, the uniform mixture is then added to the combined glycol and allowed to congeal to form the herbal pharmaceutical material.

12. The method of claim 6, wherein the solubility of the hydrophilic ointment is increased with the addition of stearyl alcohol.

13. A method of treating skin diseases, comprising the steps of:

topically applying to the affected dermis a therapeutically effective amount of a composition comprising a latex extracted from the leaves of the *Wrightia tinctoria* R. Br. plant, urea in an amount of 10% by weight as compared to the latex, and polyethylene glycol, wherein said latex is exposed to a light source emitting a light comprised of wavelengths between 300–900 nm for six to eight hours a day, during a three day period.

14. The method of claim 13, wherein the latex extract is prepared by collecting and cleaning the leaves, dicing and churning the leaves with an equal amount of water for 3 to 9 hours to form a latex slurry, exposing the slurry to a light source emitting a light comprised of wavelengths between 300–900 nm for six to eight hours a day for three consecutive days, and filtering the latex slurry.

15. The method of claim 13, wherein urea is added in portions while the urea and latex are being mixed to form a uniform mixture.

16. The method of claim 13, wherein the polyethylene glycol is a polyethylene glycol 3350 and a polyethylene glycol 400, the polyethylene glycol 3350 and the polyethylene glycol 400 are combined and heated to approximately 65° C. in a water bath to a liquid state to form a combined glycol, the combined glycol are removed from the water bath, the uniform mixture is then added to the combined glycol and allowed to congeal to form a herbal pharmaceutical material.

17. The method of claim 13, wherein the solubility of the composition is increased with the addition of a stearyl alcohol.

18. The method of claim 13, wherein the composition is applied twice daily and continuously for 6 to 8 weeks.

\* \* \* \* \*